United States Patent [19]

Horiuchi et al.

[11] Patent Number: 4,465,856
[45] Date of Patent: Aug. 14, 1984

[54] PROCESS FOR PURIFYING METHACRYLAMIDE

[75] Inventors: Masato Horiuchi, Chiba; Yoshinori Hatazaki, Kanagawa; Kouji Terada, Chiba, all of Japan

[73] Assignee: Mitsui Toatsu Chemicals, Inc., Tokyo, Japan

[21] Appl. No.: 340,597

[22] Filed: Jan. 19, 1982

[30] Foreign Application Priority Data

Jan. 20, 1981 [JP] Japan ................................. 56-5973

[51] Int. Cl.$^3$ ........................................ C07C 103/133
[52] U.S. Cl. .................................................. 564/206
[58] Field of Search ........................................ 564/206

[56] References Cited

U.S. PATENT DOCUMENTS

| | | | |
|---|---|---|---|
| 2,683,173 | 7/1954 | Weirgerber | 564/206 |
| 2,753,375 | 7/1956 | Webb et al. | 564/206 |
| 2,798,887 | 7/1957 | Bikales | 564/206 |
| 2,806,881 | 9/1957 | Porter, Jr. | 564/206 |
| 3,008,990 | 11/1961 | Weiss | 564/206 |
| 3,274,245 | 9/1966 | Bobsein et al. | 564/206 |
| 3,947,518 | 3/1976 | Ohshima et al. | 564/206 X |

Primary Examiner—Robert V. Hines
Attorney, Agent, or Firm—Sughrue, Mion, Zinn, Macpeak, and Seas

[57] ABSTRACT

In a conventional process for the purification of crude methacrylamide by the recrystallization from an aqueous medium, pH of the aqueous methacrylamide solution is controlled to a value in alkaline range of at least 8 and then methacrylamide is crystallized out. As the alkali used for the pH control, there have been used alkali metal and alkaline earth metal carbonates and hydroxides. Methacrylamide to be recrystallized is crude methacrylamide obtained by neutralizing methacrylamide sulfate obtained from acetone cyanhydrin and sulfuric acid with ammonia in the presence of water.

10 Claims, No Drawings

PROCESS FOR PURIFYING METHACRYLAMIDE

BACKGROUND OF THE INVENTION

The present invention relates to a process for purifying methacrylamide by the recrystallization from an aqueous medium.

For the preparation of methacrylamide, various processes have been known. Among them, the most inexpensive and easy process comprises neutralizing methacrylamide sulfate obtained from aceton cyanhydrin and sulfuric acid. This process has been disclosed in the specifications of Japanese Patent Publications Nos. 26094/69, 2566/70 and 35885/72.

Though methacrylamide prepared by the above process is sufficiently usuable as a fiber modifier, paper-converting agent or starting material of an emulsion, it cannot be used as it is mainly as a resin modifier for a photosensitive resin, windshield, photographic film or coagulant the demand of which has been increased recently.

A reason therefor is that a quite high transparency is required of the above resin products and, therefore, the contamination of the resin with even only a very small amount of impurities which reduces the transparency must be avoided as far as possible. In other words, an extremely high transparency such as no turbidity or a high see-through of a solution of methacrylamide used as the modifier is required. If such impurities are incorporated therein even in a very small amount, the cross-linking reaction or polymerization reaction of the resin to be modified is significantly inhibited in many cases.

Transparency of the solution is an important criterion of the quality to know whether the solution is useful for said purpose or not. It has been said from experiences that a see-through described below of at least 50° is required for this purpose. However, methacrylamide available on the market does not satisfy the condition of transparency such as the above see-through at all.

The most simple and practical process for the purification of methacrylamide comprises recrystallizing methacrylamide from water or ammonia liquor (see, for example, the specification of Japanese Patent Publication No. 35885/1972). However, according to the inventors' experiments, when methacrylamide is recrystallized by the above general process, the most important transparency of the solution is hardly improved and, therefore, it cannot be used in the fields in which the above high quality is necessitated, though purity and chromaticity of methacrylamide are improved by the recrystallization.

As the impurities which contaminate methacrylamide, there may be mentioned various, inorganic and organic substances. Among those impurities, inorganic salts such as ammonium sulfate formed in the course of the neutralization can be removed relatively easily by an ordinary recrystallization process. However, it is quite difficult to remove polymers which are the main cause of the reduction of transparency. Reasons therefor are as follows: The polymers contained in the aqueous solution are too fine to be filtered and, therefore, incorporated again in methacrylamide recrystallized. Further, the polymers are water-soluble and, therefore, a great part thereof is crystallized out in the recrystallization of methacrylamide. Accordingly, the polymers cannot be removed completely by the recrystallization from water.

SUMMARY OF THE INVENTION

The object of the present invention is to provide a process for purifying methacrylamide by the recrystallization from an aqueous solvent to obtain highly transparent methacrylamide having a high quality.

The present invention provides a process for purifying methacrylamide by recrystallizing methacrylamide from its aqueous solution, characterized by controlling pH of the aqueous methacrylamide solution to a value in alkaline range of at least 8 and crystallizing methacrylamide out.

DETAILED DESCRIPTION OF THE INVENTION

Methacrylamide to be recrystallized by the process of the present invention may be produced by any method. However, it is preferred generally to be methacrylamide produced by an ordinary method wherein 1 mole of acetone cyanhydrin is reacted with 1.3–1.8 moles of concentrated sulfuric acid at an amidation temperature of 130°–170° C. to form methacrylamide sulfate, then methacrylamide sulfate is neutralized with ammonia in the presence of water so that pH of the system upon completion of the neutralization is in the range of 1–7, and thus obtained crude methacrylamide is washed with 30–200 parts of cold water per 100 parts of crude methacrylamide.

The process of the present invention for recrystallizing methacrylamide will be shown below. Fundamentally, this process is the same as usual recrystallization process. The recrystallization comprises roughly the steps of dissolving methacrylamide in an aqueous solvent at an elevated temperature, controlling pH of the aqueous methacrylamide solution, filtering insoluble matter out, crystallizing methacrylamide (usually by cooling), centrifugating the crystal, washing crystalline methacrylamide and drying the same. In the dissolution of methacrylamide at an elevated temperature, water is used as the solvent and methacrylamide is dissolved therein at a dissolution temperature in the range of 30°–60° C., preferably 40°–55° C. A reason therefor is that if the dissolution temperature is higher than the above range, methacrylamide is apt to be polymerized and, on the other hand, if said temperature is lower than the above range, solubility of methacrylamide is reduced, the crystal obtained in the crystallization step is small in amount and the efficiency is reduced. Solubilities of methacrylamide are about 25–70 wt. % at a dissolution temperature of 30°–60° C. And about 35–59 wt. % at 40°–55° C. From the viewpoint of the transfer of the liquid to the next step, the most preferred embodiment comprises conditions of a dissolution temperature of 50° C. and a dissolution concentration of 35–40 wt. %.

Then hydrogen ion concentration in the aqueous methacrylamide solution is controlled to an alkaline range of at least 8, preferably at least pH 9, particularly at least pH 10. If the pH value is below 8, resulting methacrylamide has a see-through lower than the above desired range. As shown in examples given below, transparency of methacrylamide is increased as alkalinity of the aqueous solution is elevated in said range of above pH 8. Accordingly, in case methacrylamide of a higher quality is to be obtained, pH of the aqueous methacrylamide solution is controlled to a suitable ph of, for example, higher than 9, higher than 10 or higher than 12. However, it is to be noted in this connection that even if the alkalinity is increased excessively to, for example, abover pH 13, the transparency is no more improved but the alkali used for pH control is increased in amount in vain.

As the alkali used for pH control according to the present invention, any alkali may be used without limitation. The alkali may be selected suitably according to degree of pH control required and availability thereof. Generally, carbonates and hydroxides of alkali metals and alkaline earth metals as well as ammmonia are used. Among them, an aqueous sodium or potassium hydroxide solution is preferred. The time of pH control is not limited to directly after the dissolution of methacrylamide but it is requested only that pH of the aqueous methacrylamide solution before the crystallization is within said range.

Thereafter, an insoluble matter in the aqueous acrylamide solution is filtered out. As a matter of course, this step may be omitted when the amount of the insoluble matter is very small.

Then, methacrylamide is crystallized out from the clear aqueous methacrylamide solution. The crystallization may be effected by any of ordinarily employed methods in the present invention. However, in view of a solubility curve of methacrylamide, the crystallization by cooling is preferred. Any specific crystallization device is not particularly required, since crystals of methacrylamide having a relatively large diameter can be obtained easily by the crystallization. The aqueous methacrylamide solution may be cooled by either indirect cooling method (method wherein the solution is cooled by means of a cooling surface of a jacket or coil) or adiabatic cooling method. It is preferred that air or oxygen having an effect of preventing the polymerization of unsaturated compound is present in the crystallization tank, since methacrylamide is easily polymerized. From this point of view, the indirect cooling method is preferred, since dissolved oxygen is reduced in amount in the vacuum adiabatic cooling method. The cooling temperature is not particularly limited. However, the solution is cooled preferably to a range of 0°–25° C., practically 10°–20° C.

In order to inhibit the polymerization of methacrylamide, it is preferred to introduce a small amount of air over the whole steps ranging from the dissolution of methacrylamide to the crystallization.

Methacrylamide crystallize out is separated from the aqueous solution by an ordinary method such as centrifugation. The mother liquid containing a very small amount of salts such as ammonium sulfate is still attached to the methacrylamide crystal thus separated out. It is, therefore, preferred to wash the crystal with a small quantity of cold water. The quantity of water used for the washing is amount 30–50 parts per 100 parts of methacrylamide to effect the sufficient washing. The aqueous solution (mother liquor remaining after the recrystallization) and the washing solution may be used again as water (aqueous solvent) in which methacrylamide is to be dissolved in the next step. Resulting methacrylamide crystal may be dried by an ordinary method.

The process of the present invention may be carried out either continuously or batchwise.

The see-through and turbidity employed as the criteria in the estimation of quality of methacrylamide are measured as shown below:

See-through was determined according to JIS K 0102-1974 [Test Methods of Plant Waste Water; 6. See-Through (p. 14)]. The term "vision-through" herein indicates a degree of clearness of a sample. A sign of double cross on a sign-board was seen through a sample from the top of a see-through meter. Depth of water in the tank was measured when it became possible to clearly distinguish the double cross at the bottom of the meter. 1 cm of the height was shown by 1°. The see-through meter is shown in FIG. 17 on page 14 of the JIS specification. A commercially available see-through meter having 50 cm calibration was used in our experiments.

Turbidity was determined as follows: Kaolin was used as a standard reagent. A coefficient was determined from the relationship between kaolin concentration and absorbance. Turbidity was calculated by multiplying an absorbancy of 10% aqueous methacrylamide solution by the coefficient. A turbidity of 1 mg/l of kaolin was shown by 1°. The absorbance of 10% aqueous methacrylamide solution was measured by means of a photoelectric photometer and shown by $-\log T$. Wave length employed was 610 nm.

As for the qualities of methacrylamide (excluding water) obtained by the process of the present invention, purity was 99.7–99.9%, Hazen number (APHA) of 10% aqueous solution was less than 5, see-through of a solution obtained by dissolving 100 g of methacrylamide in 320 ml of methanol had a see-through of at least 50° and inorganic salt (such as ammonium sulfate) content of less than 10 ppm. It was impossible to measure a see-through of higher than 5°, since the graduation of the see-through meter was up to 50 cm. However, a see-through of higher than 50° and sometimes higher than 100° can be obtained by measuring an absorbance of the solution by means of the photoelectric photometer and determining the see-through from the interrelationship between the absorbance ($-\log T$) and see-through by the extrapolation. Methacrylamide thus purified can sufficiently be used for the purpose of which a high quality is required.

The following examples and comparative examples will further illustrate the present invention.

The analysis methods employed in the examples and comparative examples were as shown below:

Purity: A double bond value was determined by the bromination titration method. Methacrylic acid contained in a small amount in methacrylamide was analyzed by the gas chromatography and the resulting value was deducted from the double bond value.

Hazen number (APHA): Hazen number of 10% aqueous methacrylamide solution was determined by a colorimetric method according to ASTM D-1209-62 using a color of an aqueous $K_2PtCl_6\text{-}CoCl_2\cdot 6H_2O$ solution as the standard color. Methods of determining absorbancy, turbidity and see-through were as shown above. Inorganic salts were determined by analyzing sulfuric acid radical and totally represented as ammonium sulfate.

EXAMPLE 1

1.4 l of water was charged in a 3 l beaker provided with a stirrer and immersed in water. It was heated to 50° C. and added with 754 g of methacrylamide obtained in Comparative Example 1. The temperature was elevated to 48° C. over 20 minutes to dissolve methacrylamide. Then, 10% aqueous sodium hydroxide solution was added dropwise thereto to adjust it to pH 12. In the course of this procedure, a float type flow meter (KG 2; a product of Kusano Kagaku Kikai Seisaku-sho) was used and air was introduced at a graduation of 100.

Then, the aqueous methacrylamide solution was rapidly filtered through a Nutsche funnel provided with a No. 5 quantitative filter paper. The aqueous methacrylamine solution was cooled to 20° C. over 30 minutes by means of an ice-cooling bath under stirring to crystallize methacrylamide out. Methacrylamide was separated out from the resulting slurry by means of a centrifugal separator having an inner diameter of 15 cm and then washed with water by spraying 180 ml of water (15° C.) by means of a spray nozzle. After effecting the dehydration sufficiently, resulting methacrylamide was charged in a 1 l eggplant type flask immersed in a water bath at 70° C. and dried under reduced pressure by means of a rotary evaporator under an inner pressure of 50 mm Hg over 20 minutes to obtain 340 g of methacrylamide having a water content of 0.30% determined by Karl Fischer's method. 10% Aqueous methacrylamide solution had pH 6.7. Analytical values of methacrylamide are shown in Table 1. Purity et al. were calculated on dry (water-free) basis.

EXAMPLES 2 and 3

The same experiments as in Example 1 were repeated except that pH value was converted to 9 or 8. Methacrylamide thus obtained had a water content of 0.30%. The analytical values obtained are shown in Table 1.

COMPARATIVE EXAMPLE 1

974 ml of water was charged in a 3 l beaker provided with a stirrer and immersed in a water bath. 739 g of methacrylamide sulfate having an amidation degree of 93.5% produced under conditions comprising a sulfuric acid/acetone cyanhydrin molar ratio of 1.7 and amidation temperature of 160° C. was added dropwise thereto at a liquid temperature of up to 30° C. Then, 169 g of ammonia gas obtained by gasifying liquid ammonia was introduced therein under cooling with ice over one hour while the liquid temperature was kept at 40°–45° C. to effect the neutralization. Thus obtained slurry was subjected to the centrifugation in the same manner as in Example 1. The solid was washed by spraying 240 g of water (15° C.), dehydrated and dried in the same manner as in Example 1 to obtain 182 g of methacrylamide having a water content of 0.32%. The analytical values are shown in Table 1.

COMPARATIVE EXAMPLE 2

The same experiments as in Example 1 were repeated except that an aqueous sodium hydroxide solution was used for the pH control. Methacrylamide thus obtained had a water content of 0.35%. The analytical values are shown in Table 1.

COMPARATIVE EXAMPLE 3

The same experiments as in Example 1 were repeated except that pH was controlled to 7. Methacrylamide thus obtained had a water content of 0.34%. The analytical values are shown in Table 1.

It is apparent from Table 1 that as compared with methacrylamide purified in the above comparative examples, methacrylamide purified by the process of the present invention had superior qualities with respect to the all properties examined, particularly see-through.

TABLE 1

| Item | Example 1 | Example 2 | Example 3 | Comparative Example 1** | Comparative Example 2 | Comparative Example 3 |
|---|---|---|---|---|---|---|
| pH of aqueous solution before the crystallization | 12 | 9 | 8 | — | 4.5 | 7 |
| Purity (%) | 99.8 | 99.7 | 99.7 | 99.3 | 99.7 | 99.7 |
| Hazen number (APHA) | lower than 5 | 5 | 7.5 | 20 | 15 | 12.5 |
| Absorbance (−log T) | 0.009 | 0.014 | 0.026 | 0.086 | 0.047 | 0.040 |
| Turbidity (degrees) | 1.6 | 2.5 | 4.6 | 15.1 | 8.2 | 7.0 |
| See-through (degrees) | higher than 100 | higher than 100 | 60 | 3 | 10 | 12 |
| Inorganic salts (ppm) | 10 | 16 | 16 | 3500 | 20 | 18 |

*Values of higher than 50 were obtained by the extrapolation.
**Methacrylamide to be recrystallized.

What is claimed is:

1. A process for purifying methacrylamide by recrystallizing crude methacrylamide from an aqueous solution thereof which comprises controlling the pH of the aqueous solution to an alkaline pH of at least 8 and then crystallizing methacrylamide out.

2. A process according to claim 1 which comprises dissolving the methacrylamide in an aqueous solvent at a temperature of 30° to 60° C., controlling the pH of the resulting aqueous methacrylamide solution to at least 8, crystallizing methacrylamide by cooling, centrifuging the resulting methacrylamide crystals, washing the resulting methacrylamide crystals and drying the resulting methacrylamide crystals.

3. A process according to claim 1 wherein the pH is controlled to be in the range of from 8 to 13.

4. A process according to claim 3 wherein the pH is at least 9.

5. A process according to claim 3 wherein the pH is at least 10.

6. A process according to claim 1 wherein the methacrylamide product illustrates increased transparency.

7. A process according to claim 1 wherein and alkali is used for the pH control which is selected from the group consisting of alkali metal and alkaline earth metal carbonates and hydroxides and ammonia.

8. A process according to claim 1 wherein the methacrylamide to be recrystallized is crude methacrylamide obtained by neutralizing methacrylamide sulfate obtained from acetone cyanhydrin and sulfuric acid with ammonia in the presence of water.

9. A process according to claim 1 wherein the crystallization is carried out by and indirect cooling method.

10. A process according to claim 9 wherein the cooling temperature is in the range of 0°–25° C.

* * * * *